(12) United States Patent
Chotenovsky

(10) Patent No.: US 7,546,856 B2
(45) Date of Patent: Jun. 16, 2009

(54) ADAPTER FOR AN ANESTHETIC VAPORIZER

(75) Inventor: David J. Chotenovsky, Barrie (CA)

(73) Assignees: Baxter International Inc., Deerfield, IL (US); Baxter Healthcare S.A., Wallisellen, Zurich (CH)

( * ) Notice: Subject to any disclaimer, the term of this patent is extended or adjusted under 35 U.S.C. 154(b) by 289 days.

(21) Appl. No.: 11/362,693

(22) Filed: Feb. 27, 2006

(65) Prior Publication Data

US 2007/0199616 A1   Aug. 30, 2007

(51) Int. Cl.
B65B 1/04 (2006.01)

(52) U.S. Cl. .................. 141/352; 141/291; 141/293

(58) Field of Classification Search .............. 141/351, 141/352, 291, 293; 251/149–149.7
See application file for complete search history.

(56) References Cited

U.S. PATENT DOCUMENTS

| | | | |
|---|---|---|---|
| 5,144,991 A | 9/1992 | Wallroth et al. | |
| 5,287,898 A | 2/1994 | Falb et al. | |
| 5,427,145 A | 6/1995 | Grabenkort | |
| 5,505,236 A * | 4/1996 | Grabenkort et al. | 141/329 |
| 5,617,906 A | 4/1997 | Braatz et al. | |
| 5,682,874 A | 11/1997 | Grabenkort et al. | |
| 5,687,777 A | 11/1997 | Dobson et al. | |
| 5,810,001 A | 9/1998 | Genga et al. | |
| 5,915,427 A | 6/1999 | Grabenkort | |
| 6,585,016 B1 * | 7/2003 | Falligant et al. | 141/352 |
| 6,676,172 B2 | 1/2004 | Alksnis | |
| 6,745,800 B1 | 6/2004 | Sansom | |
| 6,817,390 B2 | 11/2004 | Falligant et al. | |
| 6,929,041 B2 | 8/2005 | Falligant et al. | |
| 2003/0075241 A1 | 4/2003 | Videbrink | |
| 2006/0048842 A1 | 3/2006 | Bunke et al. | |
| 2006/0130930 A1 * | 6/2006 | Turker et al. | 141/351 |

FOREIGN PATENT DOCUMENTS

| | | |
|---|---|---|
| DE | 10 2004 043 652 B3 | 10/2005 |
| EP | 0 678 042 B1 | 12/2000 |
| EP | 0 720 494 B1 | 3/2002 |
| EP | 0 754 071 B1 | 9/2002 |
| EP | 0 805 698 B1 | 4/2003 |
| EP | 1 304 132 A1 | 4/2003 |
| EP | 0 954 349 B1 | 10/2003 |
| FR | 2 879 466 A1 | 6/2006 |
| WO | 2005/056093 A1 | 6/2005 |
| WO | PCT/US2007/062728 | 7/2007 |

* cited by examiner

*Primary Examiner*—Timothy L Maust
*Assistant Examiner*—William McCalister
(74) *Attorney, Agent, or Firm*—Jeffrey C. Nichols; Joseph P. Reagen; Austin J. Foley

(57) ABSTRACT

An adapter is provided with a base mountable on a bottle containing a liquid anesthetic agent. A spout extending upwardly from the base is received by an inlet port of an anesthetic vaporizer having a movable valve assembly and a stationary portion, such as a radial ledge. The spout includes a stationary contact member configured to contact and open the vaporizer valve assembly when the spout is inserted into the inlet port. The adapter also includes a movable valve assembly that is contacted and opened by the stationary portion of the inlet port when the spout is inserted into the inlet port. The contact member and adapter valve assembly are arranged such that, when the spout is inserted into the inlet port, the contact member opens the vaporizer valve assembly before the stationary portion of the inlet port opens the adapter valve assembly.

15 Claims, 8 Drawing Sheets

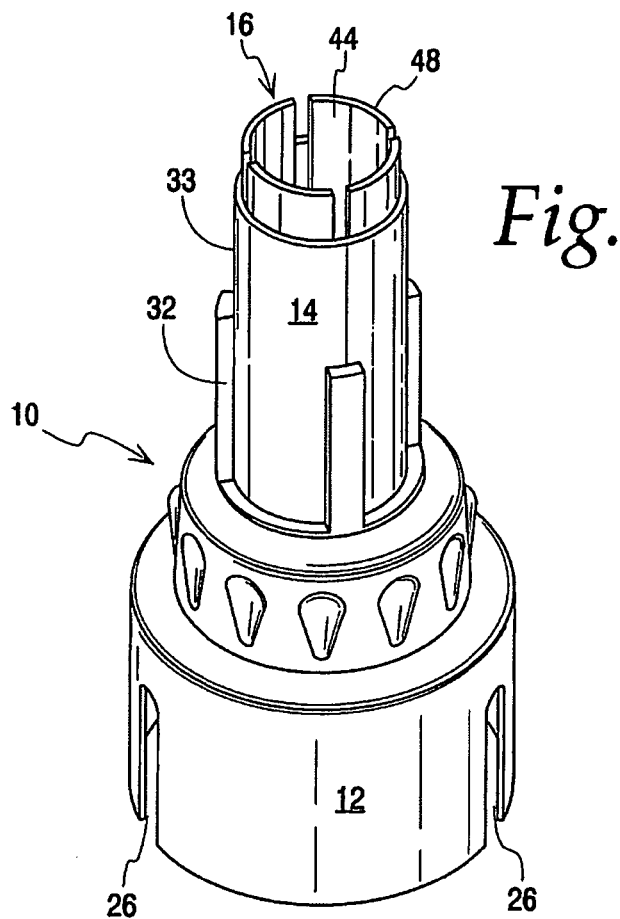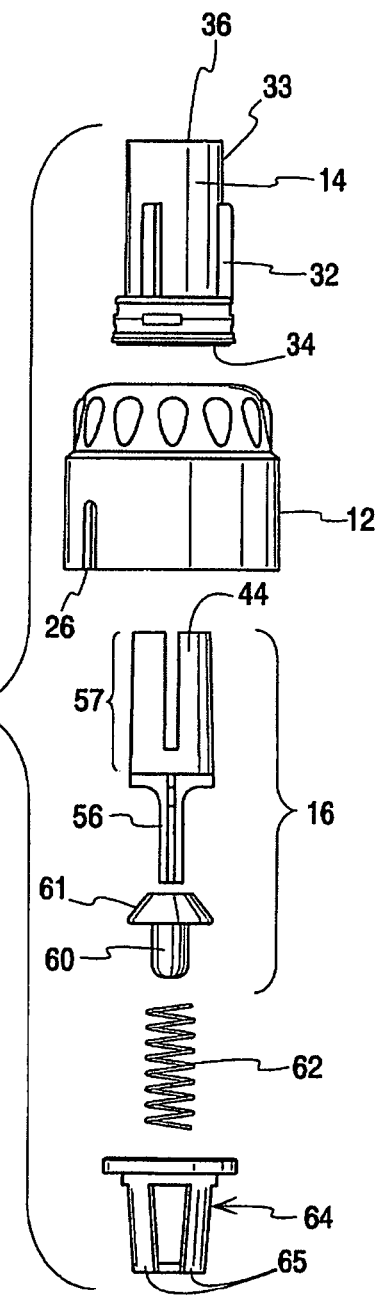
*Fig. 1A*
*Fig. 1B*

ADAPTER FOR AN ANESTHETIC VAPORIZER

BACKGROUND OF THE INVENTION

1. Field of the Invention

This invention generally relates to apparatus for allowing selective fluid communication between an anesthetic agent container and an anesthetic vaporizer. More particularly, the invention relates to an adapter mountable on an anesthetic agent container for connecting the container to an inlet port of an anesthetic vaporizer.

2. Description of Related Art

During surgical procedures, it often is necessary to anesthetize a patient. One method of delivering anesthetic is in a gaseous form, which is inhaled by the patient. For the safety of the patient and medical personnel, the anesthetic agent is typically transported in liquid form in a suitable container. Known liquid anesthetics include halothane, isoflurane, and sevoflurane. The liquid anesthetic is ultimately dispensed into an anesthetic vaporizer, which mixes the liquid anesthetic agent with a carrier gas, such as oxygen or nitrous oxide, that is inhalable by a patient.

Liquid anesthetics are relatively volatile and can evaporate at room temperature. Before it can be used, the anesthetic agent must be transferred from a first closed environment, e.g., a container or bottle, to a second closed environment, e.g., a vaporizer. In order to transfer the anesthetic, it is well-known to provide a vaporizer inlet port with a valving system that is selectively openable to allow a liquid anesthetic agent to be poured into an internal sump of the vaporizer. Such valving systems for sevoflurane are described in U.S. Pat. No. 5,381,836 to Braatz et al. and in U.S. Pat. No. 5,505,236 to Grabenkort et al., which are hereby incorporated herein by reference. The system described in Grabenkort et al. is understood to be commercially referred to as the Quik-Fil™ system of Abbott Laboratories, and similar systems can be found in numerous vaporizers, such as the Sevotec 5™ vaporizer from Datex-Ohmeda, Inc.

The above patents describe an arrangement in which the anesthetic agent container is provided with an integral or separate adapter with a valving system configured to mate with the vaporizer valving system for allowing selective dispensing of the liquid anesthetic contained therein. To transfer anesthetic agent from the container to the vaporizer, the adapter is inserted into the vaporizer inlet port. As a result of competing biasing springs in the adapter and the vaporizer, insertion of the adapter results in sequential opening of a valve associated with the inlet port of the vaporizer and a valve associated with the adapter, allowing the liquid anesthetic agent to flow out of the container, through the adapter, and into the vaporizer sump. Thereafter, the adapter and container are removed from the vaporizer inlet port and the adapter valving system and vaporizer valving system are separately, automatically closed by the biasing springs.

One potential drawback with the filling systems of Braatz et al. and Grabenkort et al. is that they rely on the proper selection and quality control of competing biasing springs of different strength in the adapter and vaporizer valving systems in order to cause the preferred sequential opening of the vaporizer before the adapter. Of course, this system does not work properly if the springs, through lack of manufacturing quality control or for other reasons, are not of the proper strength. Accordingly, attempts have been made to provide alternative filling systems. One example of an alternative filling system is described in U.S. Pat. No. 6,585,016 to Falligant et al., which is hereby incorporated herein by reference. Variations of the Falligant filling system are described in U.S. Pat. Nos. 6,817,390 and 6,929,041, both to Falligant et al. and both of which are hereby incorporated herein by reference. These systems generally employ a fixed central rod or finger in the vaporizer inlet opening to directly contact a valve head in the adapter and force it open when the adapter is inserted into the vaporizer inlet opening.

While the above filling systems eliminate the need to properly select or calibrate the biasing springs, one drawback with them is that they require a different vaporizer valving system that may not be compatible with prior competing-spring systems and may result in confusion in the marketplace and among anesthesiologists or technicians.

As set forth in more detail below, the present invention provides an improved adapter that does not suffer from one or more of the above drawbacks.

SUMMARY OF THE INVENTION

This invention provides an adapter mountable on an anesthetic agent container. The adapter includes a spout configured to be received by a vaporizer inlet port having a movable vaporizer valve assembly and a stationary portion. The spout includes a stationary contact member and a movable adapter valve assembly. The contact member is configured to contact and move the movable vaporizer valve assembly when the spout is inserted into the vaporizer inlet port. The movable adapter valve assembly is opened by contact with the stationary portion of the vaporizer inlet port when the spout is inserted in the vaporizer inlet port. It will be seen that an adapter according to this aspect of the present invention eliminates competing springs and the associated drawbacks.

This invention also provides a method for transferring an anesthetic agent from an anesthetic agent container to an anesthetic vaporizer. An adapter is provided on an anesthetic agent container, which adapter includes a spout, a movable adapter valve assembly, and a substantially stationary contact member. The spout is inserted into an inlet port of the vaporizer until the stationary contact member contacts and moves a movable vaporizer valve assembly. The spout is then further inserted until a stationary portion of the vaporizer inlet port contacts and moves the adapter valve assembly, which allows anesthetic agent to flow from the container into the vaporizer. It will be seen that a method according to this aspect of the present invention allows for the sequential opening of a vaporizer valve before an adapter valve without requiring competing springs in the vaporizer and the adapter.

BRIEF DESCRIPTION OF THE DRAWINGS

FIG. 1A is a front perspective view of an adapter according to a preferred embodiment of the present invention;

FIG. 1B is an exploded view of the adapter of FIG. 1A;

DESCRIPTION OF THE PREFERRED EMBODIMENTS

Although the present invention is described as illustrated in the attached drawings of the preferred embodiment, it is to be understood that the disclosed embodiments are merely exemplary of the invention, which may be embodied in various forms. Therefore, specific details disclosed herein are not to be interpreted as limiting, but as a representative basis for teaching one skilled in the art to variously employ the present invention in virtually any appropriate manner.

Figure 1C:
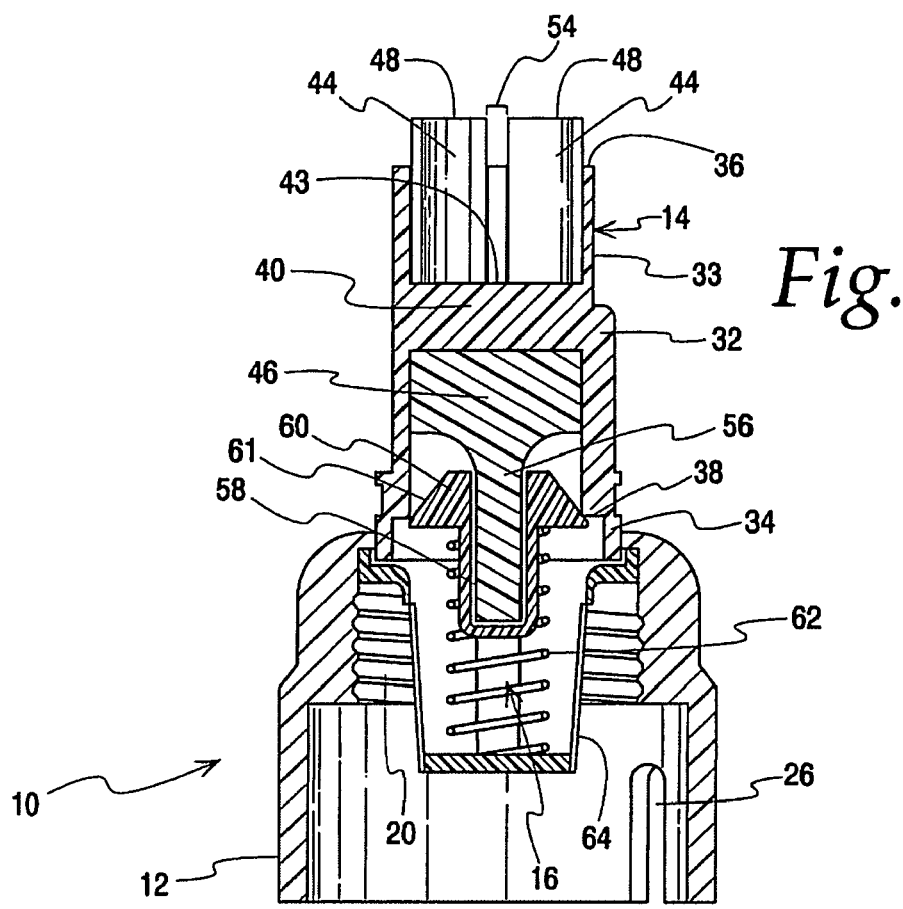
FIG. 1C is a side cross-sectional view of the adapter of FIG. 1A in a closed position.
Figure 1D:
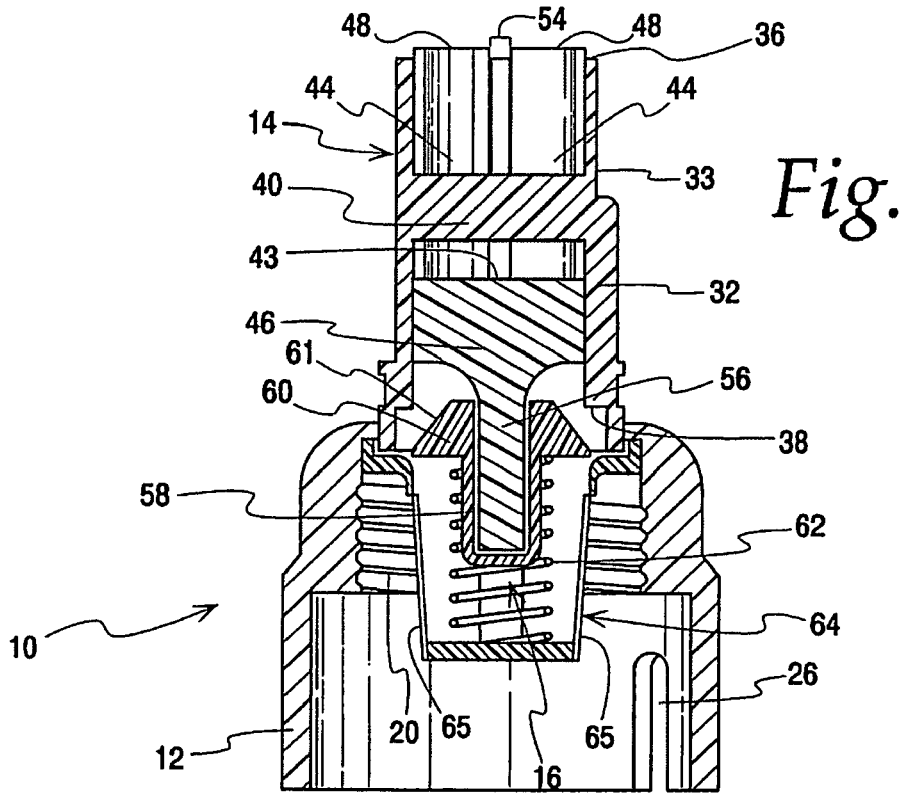
FIG. 1D is a side cross-sectional view of the adapter of FIG. 1A in an open position.
Figure 2:
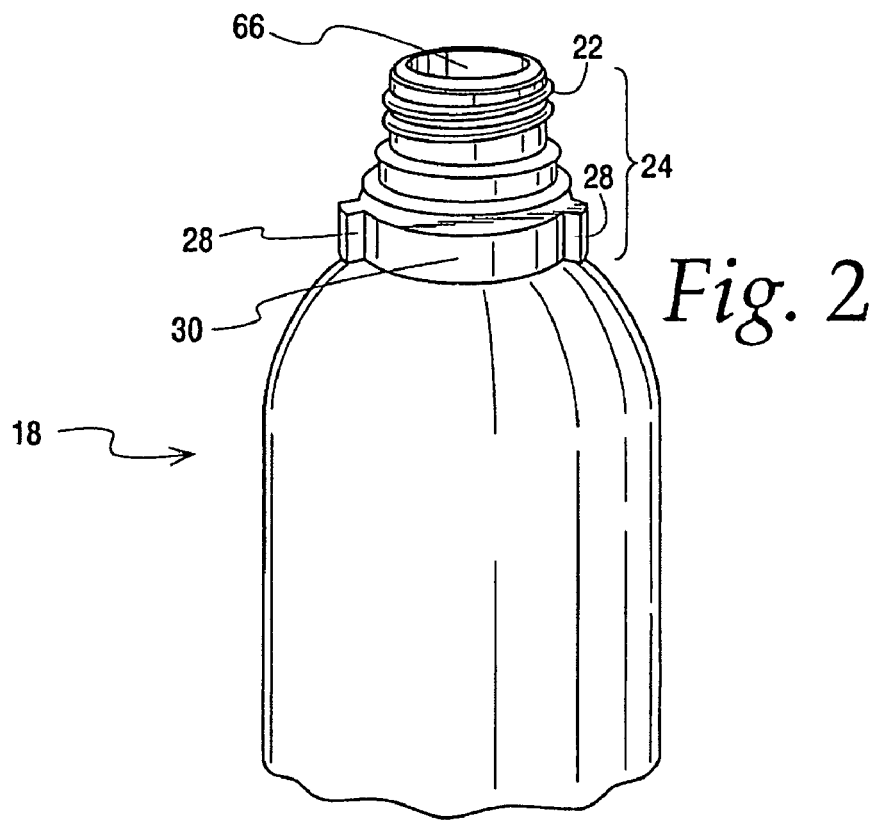
FIG. 2 is a front perspective view of a liquid anesthetic agent container suitable for use with the adapter of FIG. 1A.

FIGS. 1A-1D show an adapter according to the present invention. The adapter is generally identified as element 10 in FIGS. 1A-1D. The illustrated adapter 10 includes a base 12, a spout 14, and a movable adapter valve assembly 16. Although illustrated as separate pieces, certain of these may be combined or molded in a single piece, if so desired. The base 12 is located at a lower end of the adapter 10 and is configured to be attached to a liquid anesthetic agent container or bottle 18, which is illustrated in FIG. 2. When used herein to describe the elements of the adapter 10 and the relative positioning of the elements, the terms "lower," "below," "bottom," "downwardly," "upper," "above," "top," "upwardly," and variations thereof are intended to describe the orientation as illustrated in FIGS. 1A-1D.

The base 12 is preferably molded of rigid plastic and includes internal threads 20 that are configured to mate with external threads 22 on a neck portion 24 of the container 18, although other means for attachment to the container may also be used without departing from the present invention. Also, it is not required that the base and adapter be removable from the container, and they may be permanently attached while still employing the present invention.

Preferably, the base 12 also includes a pair of slots 26, both of which are illustrated in FIG. 1A, that are configured to fit over a pair of ribs 28 on a collar 30 which is rotatable on the neck 24 of the container 18. The purpose and operation of slots and ribs is to prevent the attachment of an improper anesthetic agent container to an adapter, as is well-known to those skilled in the art. The top of the base 12 has a central aperture, through which the spout 14 is inserted.

The spout 14 is a generally tubular member and extends upwardly from the base 12. The spout 14 preferably is also molded of rigid plastic and includes at least one spline 32 on its outer surface 33 for interacting with a vaporizer inlet port, as will be described herein. A bottom end 34 of the spout 14 may be press fit into the base 12 or attached to the base 12 with other suitable means or be an integral part of the base 12. In the preferred embodiment, the press fit allows the spout to rotate relative to the base. A top end or lip 36 of the spout 14 is located a selected distance above the bottom end 34 that is sufficient for insertion and interaction with the vaporizer inlet, as will be described in more detail later.

For cooperation with a valve plug discussed in more detail below, the spout 14 includes an internal annular shoulder forming a valve seat 38 adjacent to the bottom end 34. The internal annular shoulder may take various forms, such as a tapered surface or a corner edge, as best seen in FIGS. 1C and 1D, which forms a liquid seal when engaged by a valve plug.

Figure 3:
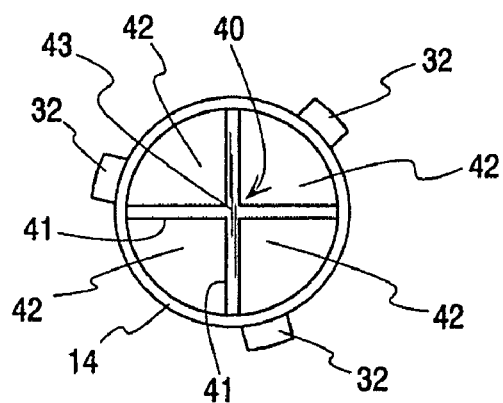
FIG. 3 is a top plan view of the spout of FIG. 1B.

The adapter 10 also includes a contact member 40. The contact member 40 is preferably attached to an interior portion of the spout 14 at a location intermediate the top end 36 and bottom end 34. The contact member 40 may be a separate piece or, more preferably, the contact member 40 may be integrally molded or otherwise formed within the spout 14. FIG. 3 illustrates the contact member 40 as being formed of a pair of diametrical, intersecting cross members or beams 41 that define a cross or "X" and divide the interior of the spout into four identical openings or quadrants 42. The exact configuration of the contact member 40 may vary, provided that the contact member 40 is substantially stationary with respect to the spout 14. At least a portion of the contact member 40 preferably extends into or is located at the center of the interior portion of the spout 14 for contacting a centrally located valve member in a vaporizer inlet. When used herein, the term "center" and its variations refer to the central axis of the tubular spout 14 for elements of the adapter 10, while referring to the central axis of a tubular vaporizer inlet port for elements of a vaporizer, which will be described in further detail herein.

The spout 14 is preferably assembled by snap fit into the central orifice or opening in the top of the base 12, extending upwardly from the base 12, as shown in FIGS. 1A-1D. Alternatively, as noted earlier, the spout 14 and base 12 may be of one-piece construction.

The adapter valve assembly 16 is movably positioned within the spout 14 and base 12 for opening and closing the adapter 10 to fluid flow therethrough. As best seen in FIGS. 1B-1D and 4B, the adapter valve assembly 16, as illustrated, includes a poppet 46 and a valve plug 60. The poppet 46 is preferably molded of a rigid plastic material and includes a lower stem portion 56 and an upper, generally cylindrical hollow or tubular portion 57. The upper cylindrical portion 57 is sized for slidable positioning within the spout 14. The cylindrical portion 57 preferably has axially extending slots 54, located 90° apart, for receiving the cross members or beams 41 of the contact member 40 located within the spout 14, and for allowing axial movement of the poppet 46 within the spout 14.

As a result of the slots 54, the wall of the upper cylindrical portion 57 is divided into four elongated members 44 forming arc segments, each of which has an arcuate extent of slightly less than 90°. When the poppet 46 is inserted into the spout 14, each elongated member 44 extends through one of the quadrants 42 formed by the intersecting beams 41 located within the spout 14. The length of the upper cylindrical portion 57 of the poppet 46 is sized so that the upper end 48 of each elongated member 44 extends beyond the stationary end 36 of the spout 14 by a selected distance when the adapter valve assembly 16 is in the closed position. As described in more detail later, when the upper ends 48 of the elongated members 44 are pushed against a stationary surface in the vaporizer inlet, the poppet 46 is forced downwardly within the spout 14, opening the adapter 10 to fluid flow therethrough. The distance by which the poppet elongated members 44 extend beyond the spout 14 may be selected as needed, but is preferably about 3-4 millimeters.

Figure 4A:
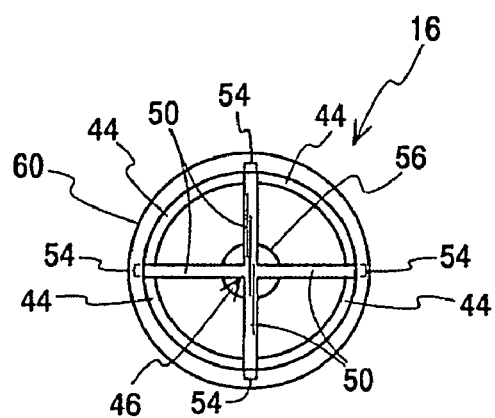
FIG. 4A is a top plan view of the adapter valve assembly of FIG. 1B.
Figure 4B:
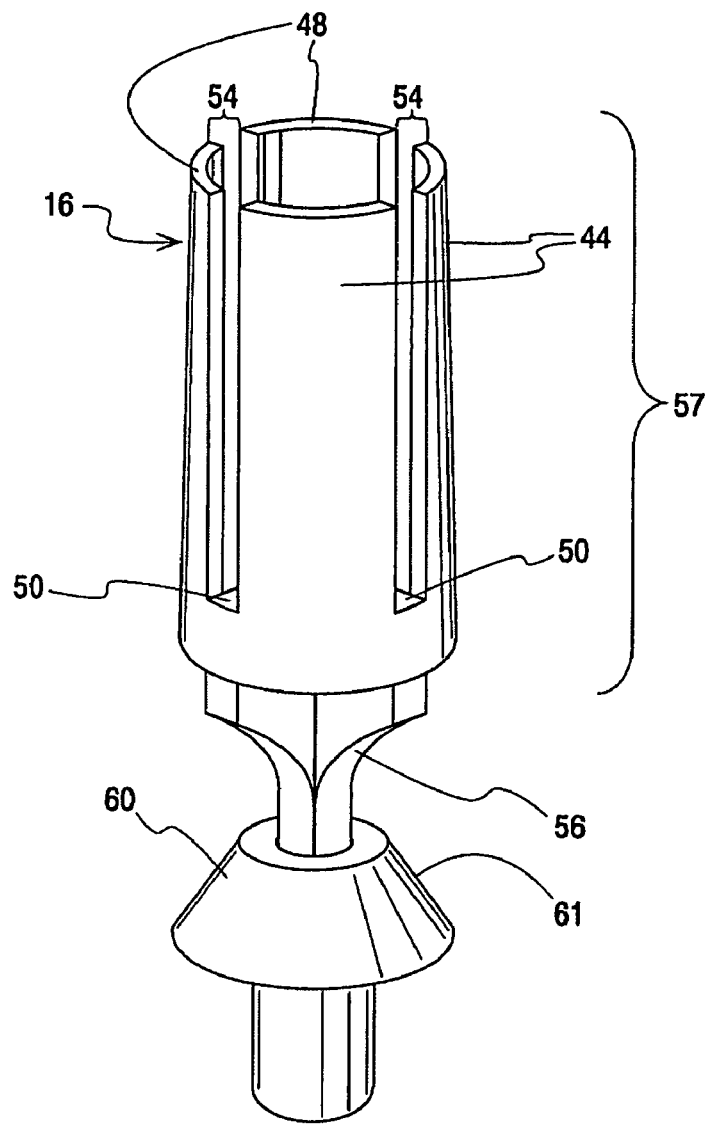
FIG. 4B is a front perspective view of the adapter valve assembly of FIG. 4A.
Figure 5:
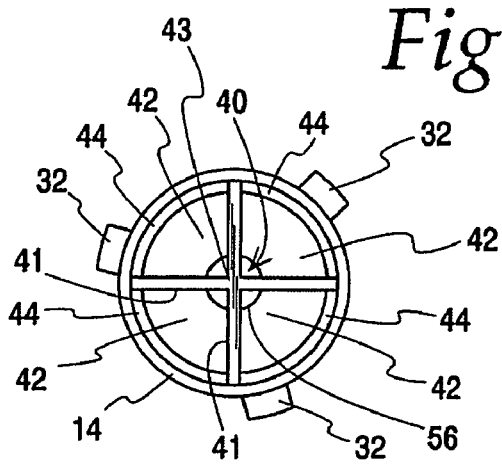
FIG. 5 is a top plan view of the adapter valve assembly of FIG. 4A assembled within the spout of FIG. 3.

The junction between the upper cylindrical portion 57 and the stem 56 of the poppet 46 is perhaps best understood by reference to FIGS. 1C, 1D, and 4A. Specifically, in the illustrated embodiment, the upper end of the stem and the lower end of the cylindrical portion terminate in four radially extending supports 50, spaced 90° apart. The area between the supports is open to allow fluid to flow through the inside of the cylindrical portion 57 and past the poppet 46. As can be seen by comparing FIGS. 3 and 4A, the configuration of the poppet supports 50 is substantially identical to the configuration of beams or cross members 41 of the spout 14. The open quadrants 42 between the supports 50 and cross members 41 allow fluid flow through the adapter 10 without significant blockage or resistance. While this configuration may be preferred, the junction of the stem 56 and cylindrical portion 57 may be of any other shape which allows fluid flow therethrough.

At the bottom of the poppet stem, the adapter valve assembly 16 includes the valve plug 60. The valve plug 60 is preferably made of resilient material, such as rubber, neoprene, or other material suitable for contact with the particular anesthetic agent and for forming a reliable seal when in contact with valve seat 38. The valve plug 60 preferably has a cylindrical cavity 58 for receiving the poppet stem 56 and a frusto-conical valve surface 61 which, as best seen in FIG. 1C, forms a straight surface for engaging the valve seat 38. The shape of the valve surface may vary as desired, but the straight, uncurved sealing surface 61 of the illustrated valve plug 60 may be preferred for engaging the valve seat 38 to block fluid flow through the adapter 10 in the closed position.

The valve plug 60 is preferably biased to a closed position as shown in FIG. 1B. In the illustrated embodiment, the valve plug 60 is biased by a coil spring 62, which is held in place by a spring retainer 64 that extends downwardly from the bottom end 34 of the spout 14. In a preferred embodiment, the spring retainer 64 is press fit onto the bottom end 34 of the spout 14, but it can be attached with any other suitable means. The spring retainer 64 extends downwardly into the base 12, so it will be received by a mouth 66 of the anesthetic agent container 18 when the adapter 10 is connected to the container 18. As best seen in FIG. 1B, the spring retainer 64 comprises spaced apart depending walls 65 that form a generally open framework. This allows anesthetic agent to flow freely through the adapter 10 when in the open position. Coil spring 62 is held in a compressed position between the bottom of the retainer 64 and the underside of valve plug 60. The force of the spring biases the valve plug 60 upwardly, pushing the frusto-conical valve surface 61 against the valve seat 38 to provide a normally closed valve position that blocks the flow of anesthetic agent through the adapter 10.

Typically, the anesthetic container 18 is provided with a twist-off cap, not illustrated, that is removed to expose an open mouth 66 into which the spring retainer 64 will pass. However, some bottles include a foil seal or other frangible membrane overlaying the mouth, which can be forcibly broken by the spring retainer 64 when the adapter 10 is attached. Alternatively, the bottom of the spring retainer may be provided with an additional cutting edge or piercing member or the like for facilitating the breaking of any frangible membrane in the container mouth.

The orientation and spacing of the elements of the adapter that determine the sequential opening of the adapter and vaporizer valve assemblies is best understood with reference to corresponding elements of an anesthetic vaporizer having a valving system and inlet port suitable for use with an adapter according to the present invention.

Figure 6:
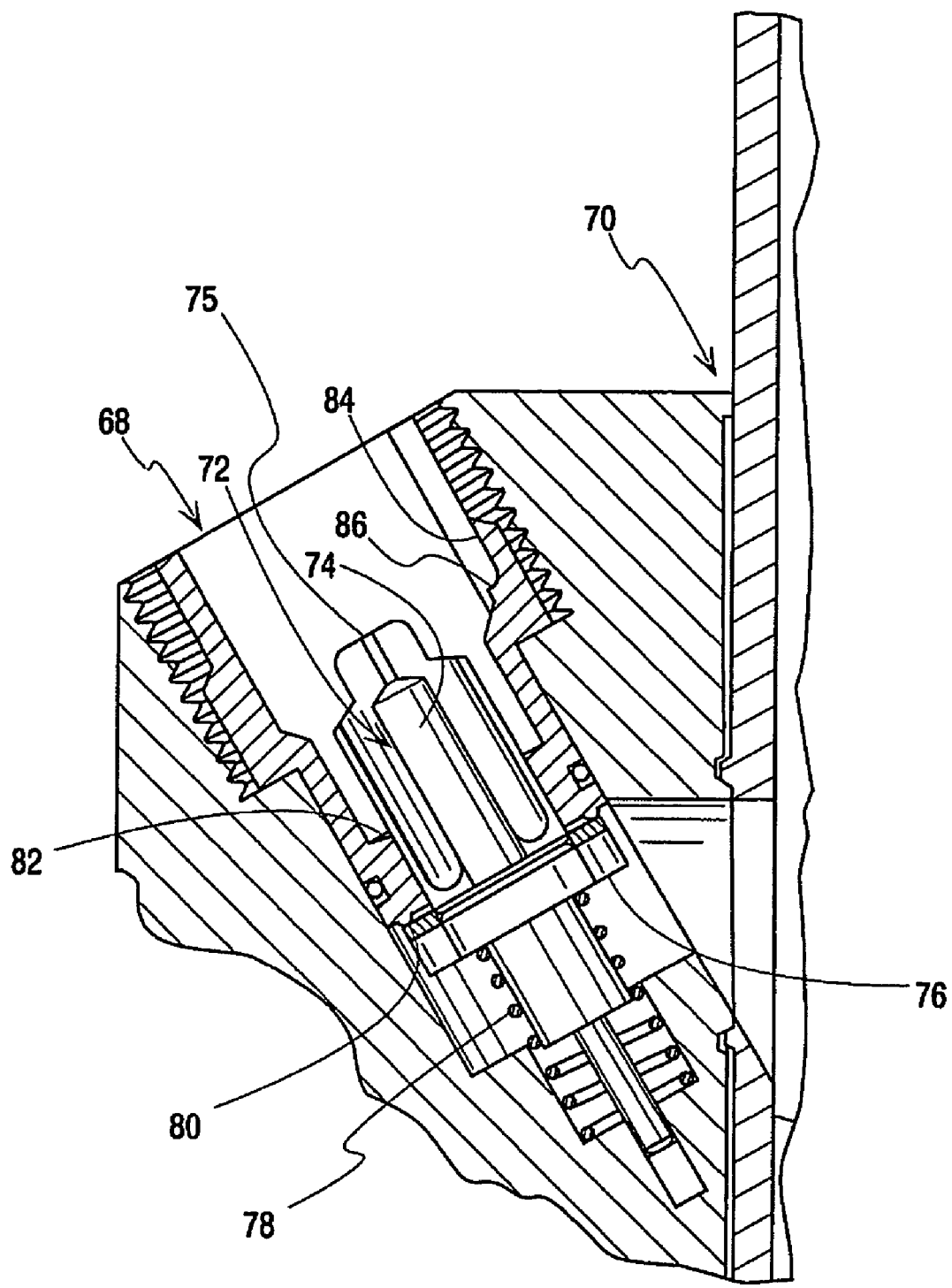
FIG. 6 is a side cross-sectional view of an anesthetic vaporizer inlet port suitable for use with an adapter according to the present invention.

For the purpose of explanation, FIG. 6 depicts an anesthetic vaporizer inlet port 68, vaporizer valve assembly 72, and other features as such are illustrated in U.S. Pat. No. 5,505,236, but it will be understood that an adapter according to the present invention also may be used in combination with other vaporizers. In particular, FIG. 6 shows a vaporizer 70 that includes an inlet port 68, which is a generally tubular, diagonally oriented passageway that allows access to an internal sump of the vaporizer.

Located within the inlet port 68 is a vaporizer valve assembly 72 that is axially movable within the inlet port 68. The vaporizer valve assembly 72 includes a central contact pin 74 having a bottom end that is associated with a vaporizer valve member 76 and movable therewith. The vaporizer valve member 76 is biased by a spring 78 into a closed position, shown in FIG. 6, to engage and seal a vaporizer valve seat 80. A force applied to the top end 75 of the contact pin 74 will push it further into inlet port 68, thereby compressing the spring 78 and unseating the vaporizer valve member 76 from the vaporizer valve seat 80 into an open position of FIG. 8.

The inlet port 68 further includes a stationary surface or portion, illustrated as a radial ledge 82, which extends around the contact pin 74. The radial ledge 82 interacts with the elongated members 44 to open the adapter valve assembly 16 of the adapter 10, as will be described herein.

Finally, the inlet port 68 may include one or more grooves 84, one of which is illustrated in FIG. 6. The interaction of the grooves 84 of the inlet port 68 and the splines 32 of the adapter 10 will be described herein.

In use, the adapter 10 is attached to a container 18 containing a liquid anesthetic agent by aligning the slots 26 of the base 12 with the ribs 28 of the collar 30, lowering the base 12 onto the mouth 66 of the container 18, and rotatably mating the internal and external threads 20 and 22. Of course, the adapter 10 may also be pre-attached to the container.

When the adapter 10 has been attached to the bottle 18, the vaporizer inlet port 68 is uncovered and the preferred single spline 32 of the spout 14 is aligned with a groove 84 of the inlet port 68. The spline 32 may be of sufficient length that it must be aligned with and received by the groove 84 before either the vaporizer valve assembly 72 or the adapter valve assembly 16 is moved to an open position. However, the spline 32 should not be configured in such a way that it prevents full insertion of the spout 14 into the inlet port 68.

Figure 8:
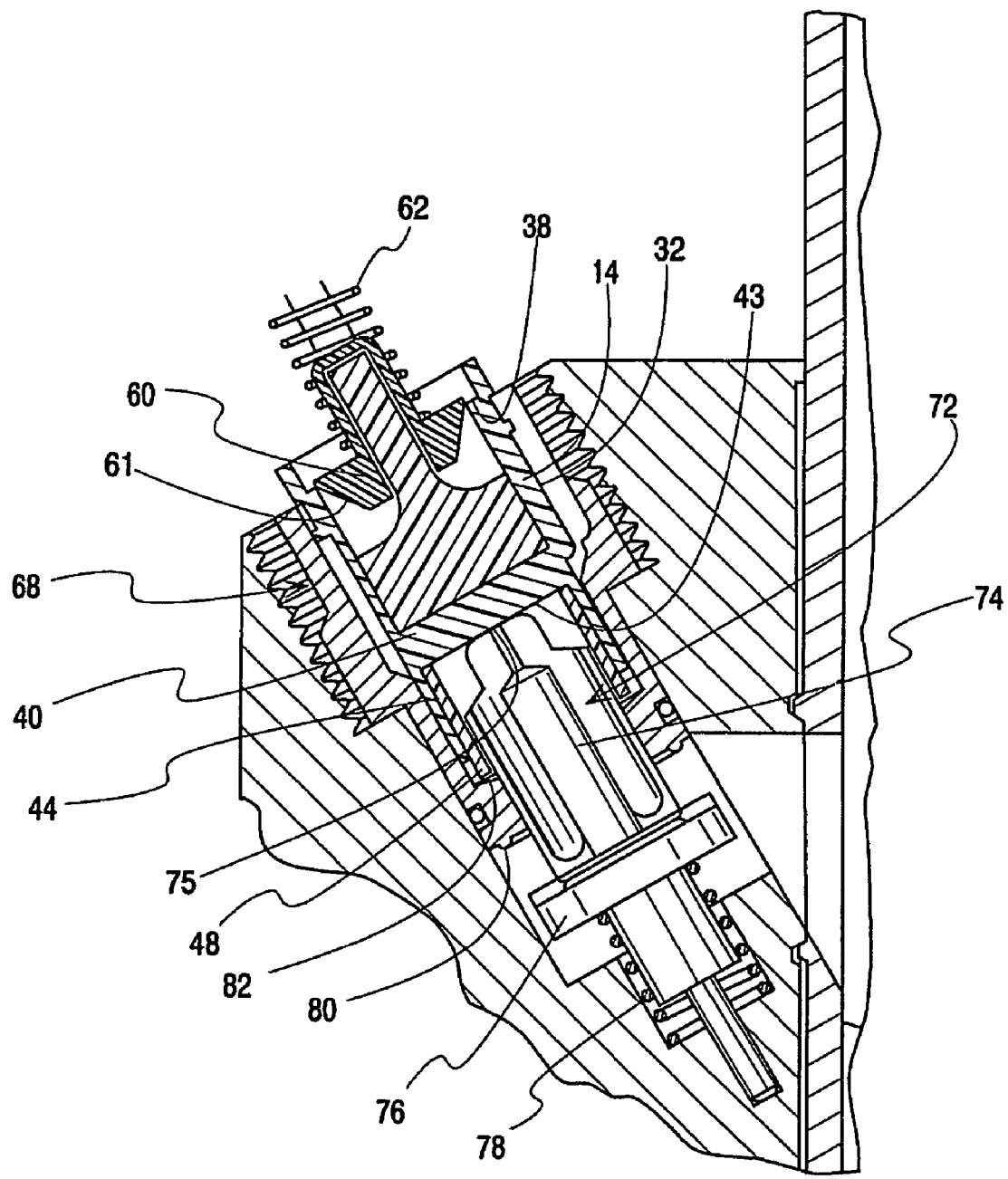
FIG. 8 is a side cross-sectional view of the inlet port and adapter of FIG. 7, with the vaporizer valve assembly in an open position, and with the adapter being further inserted into the inlet port.

If the spline 32 and groove 84 match, then the spout 14 can be further inserted into the inlet port 68 until the end surface 43 of the stationary contact member 40 located within the spout 14 contacts the end 75 of the movable contact pin 74 located within the vaporizer inlet. As the adapter 10 is inserted further, as shown in FIG. 8, the force of the stationary contact member 40 depresses the contact pin 74 into the inlet port 68, which compresses the spring 78, and moves the vaporizer valve member 76 away from the vaporizer valve seat 80 and into the open position. As may be seen in FIG. 8, the contact member 40 of the adapter 10 contacts the contact pin 74 in the vaporizer and opens the vaporizer valve assembly 72 before the elongated members 44 of the adapter valve assembly poppet 46 contact the radial ledge 82 in the vaporizer inlet 68. Thus, the spacing and orientation of the contact member 40 and elongated members 44 within the adapter 10 provide for the sequential opening of the adapter and vaporizer valves.

Figure 7:
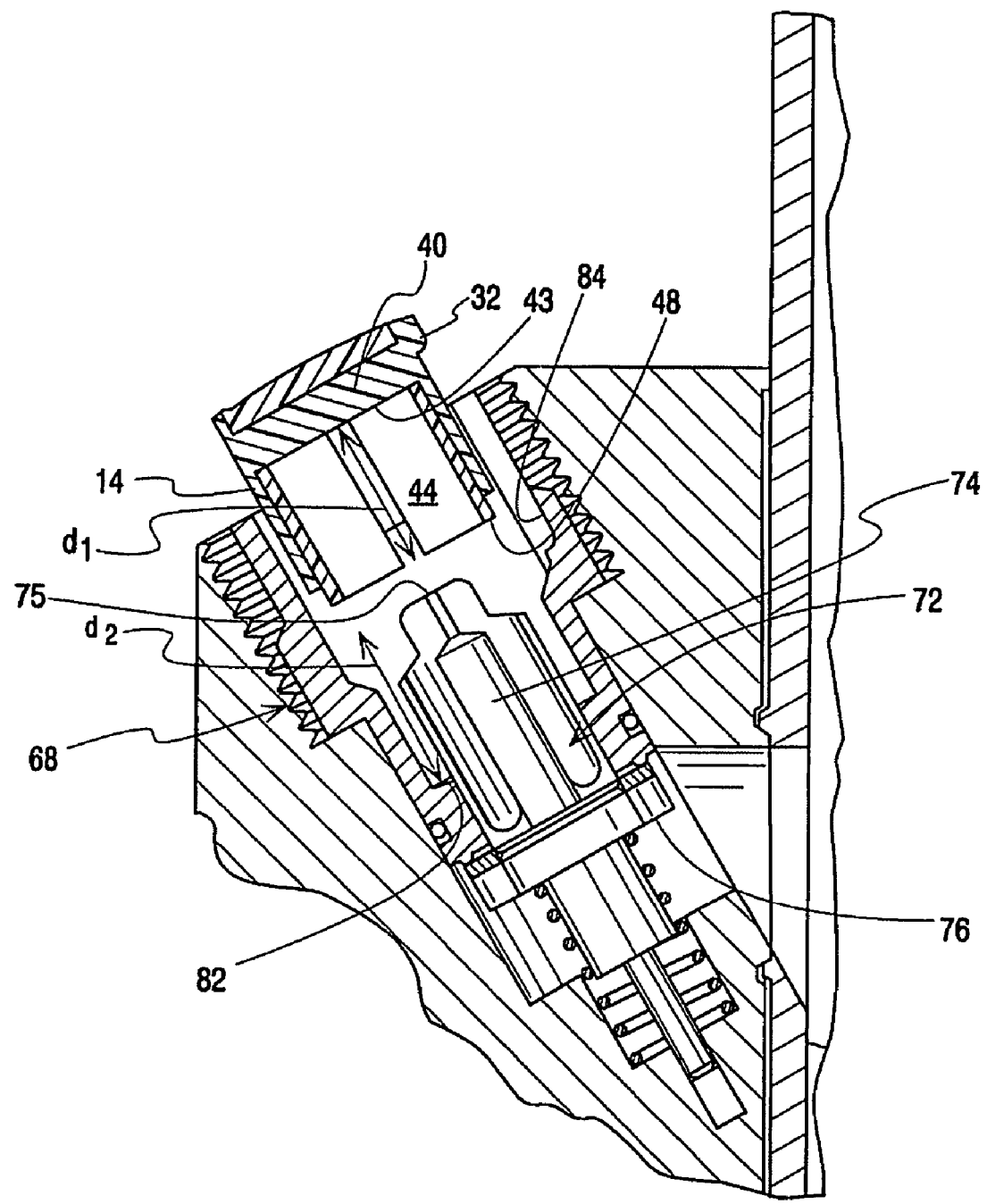
FIG. 7 is a side cross-sectional view of the anesthetic vaporizer inlet port of FIG. 6, with the vaporizer valve assembly in a closed position, and with an adapter according to the present invention being partially inserted therein.

FIG. 7 best illustrates that the axial distance $d_1$ between the upper surface 43 of the contact member 40 and the end 48 of the elongated members 44 is less than the axial distance $d_2$ between the contact end 75 of the contact pin 74 and the radial ledge 82 when the adapter valve assembly 16 and the vaporizer valve assembly 72 are in closed positions. With this spacing, the vaporizer valve assembly 72 will open before the adapter valve assembly 16 opens—otherwise liquid anesthetic agent would be allowed to pour into a closed vaporizer inlet port 68, where it could overflow or evaporate.

More specifically, in use, the adapter 10 is inserted into the vaporizer inlet until the end 75 of the contact pin 74 in the vaporizer touches the surface 43 of the adapter contact member 40. At this point, the ends 48 of the elongated members 44 are spaced from ledge 82. Continued insertion of the adapter 10 results in the stationary contact member 40 of the adapter 10 depressing the contact pin 74 of the vaporizer, thereby opening the vaporizer valve assembly 72 before the elongate members 44 contact ledge 82. Because $d_2$ is greater than $d_1$, the vaporizer valve assembly 72 is opened before the ends 48 of the elongated members 44 contact the ledge 82.

After the vaporizer valve member 76 has been moved away from the vaporizer valve seat 80 and the vaporizer valve assembly 72 has been placed in the open position of FIG. 8, the spout 14 is further inserted into the inlet port 68 until the contact ends 48 of the elongated members 44 contact the radial ledge 82. The radial ledge 82 is immobile, so further movement of the spout 14 into the inlet port 68 will force the elongated members 44 toward the container 18. This movement compresses the spring 62 in the adapter 10, which causes the adapter plug 60 to move away from the adapter valve seat 38 and places the adapter valve assembly 16 in the open position of FIGS. 1D and 9. It will be appreciated that a single elongated member 44 contacting the radial ledge 82 would provide the necessary force to open the adapter valve, but it is preferred to use multiple elongated members 44 in order to ensure that a more uniform axial force is transmitted to the adapter valve assembly 16.

Figure 9:
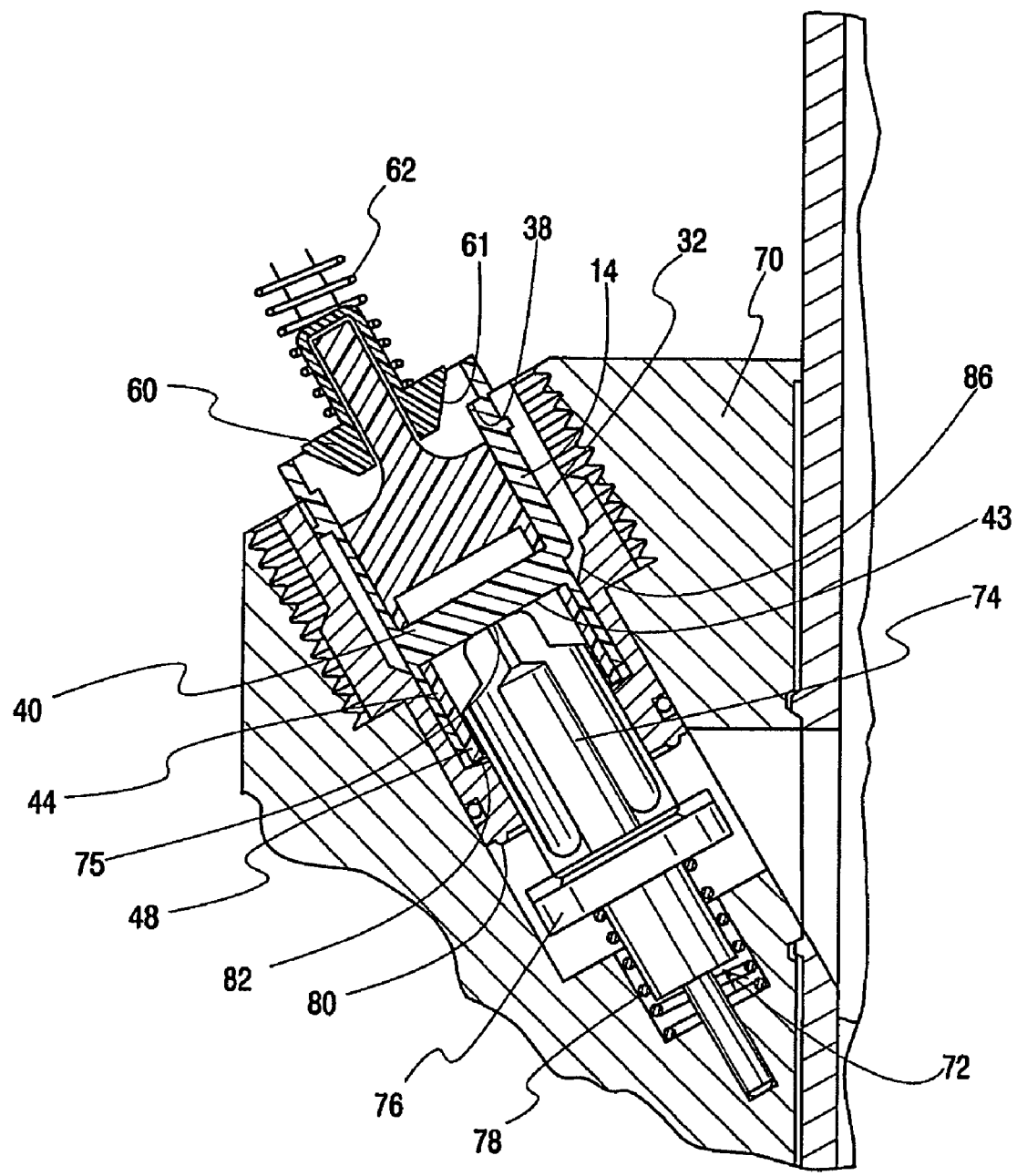
FIG. 9 is a side cross-sectional view of the inlet port and adapter of FIG. 8, with the vaporizer valve assembly in an open position, and with the adapter being even further inserted into the inlet port.

When both the vaporizer valve assembly 72 and the adapter valve assembly 16 are in the open positions shown in FIG. 9, the liquid anesthetic agent is free to flow through the adapter 10 and into the vaporizer 70. If desired, one or more of the components of the adapter 10 may be configured to define a termination point that prevents further insertion of the spout 14 into the inlet port 68 at some point after the adapter valve assembly 16 has been opened. For example, the spline 32 may have such a length that it contacts upper ledge 86 in order to prevent further insertion of the spout 14. Alternatively, the base 12 could be designed to abut the top of the inlet port 68 to prevent further insertion of the spout 14.

After the supply of anesthetic agent has been partially or fully dispensed into the vaporizer 70, the adapter 10 is removed from the inlet port 68. The removal process is the reverse of the filling process, as the adapter valve assembly 16 will move from the open position of FIG. 9 to the closed position of FIG. 8 before the vaporizer valve assembly 72 is closed. Therefore, any anesthetic agent between the adapter plug 60 and the vaporizer valve member 76 will flow past the vaporizer valve member 76 and into the vaporizer sump.

Further withdrawal of the adapter 10 from the inlet port 68 will cause the contact member 40 to disengage the contact pin 74, with the vaporizer valve assembly 72 in the closed position of FIG. 7. Finally, the adapter 10 is fully removed to place the vaporizer 70 back in its original configuration of FIG. 6.

It will be understood that the embodiments of the present invention which have been described are illustrative of some of the applications of the principles of the present invention. Numerous modifications may be made by those skilled in the art without departing from the spirit and scope of the invention, including those combinations of features that are individually disclosed or claimed herein. For these reasons, the scope of the invention is not limited to the above description but is as set forth in the following claims.

The invention claimed is:

1. An adapter mountable on an anesthetic agent container and configured to be received by an inlet port of an anesthetic vaporizer including a movable vaporizer valve assembly movable between open and closed positions, the adapter comprising:
   a base;
   a generally tubular spout extending upwardly from the base;
   a movable adapter valve assembly with an attached valve plug, the moveable adapter valve assembly further comprising an extension portion extending beyond the spout when the adapter valve is in an open and in a closed position; and
   a vaporizer valve assembly contact member which is stationary with respect to the spout and is located to contact and move the movable vaporizer valve assembly when the adapter is inserted into the vaporizer inlet port, and wherein the contact member is attached to the spout, the contact member dividing at least a portion of the interior of the spout into a plurality of openings;
   and wherein the adapter valve assembly is moved by contact with a stationary portion of the inlet port when the spout is inserted into the inlet port, and wherein the adapter valve assembly includes a plurality of elongated members configured to contact the stationary portion of the inlet port when the spout is inserted into the inlet port, and wherein each member extends through one of said openings.

2. The adapter of claim 1, wherein the contact member contacts the vaporizer valve assembly before the stationary portion of the inlet port contacts the adapter valve assembly when the spout is inserted into the inlet port.

3. The adapter of claim 1, wherein the axial distance between a contact end of the vaporizer valve assembly and the stationary portion of the inlet port when the vaporizer valve assembly is closed is greater than the axial distance between a contact end of the adapter valve assembly and a contact end of the contact member when the adapter valve assembly is in a closed position.

4. The adapter of claim 1, wherein the inlet port includes a groove and the adapter includes a spline, and wherein the groove must receive the spline before the vaporizer valve assembly is contacted by the contact member.

5. The adapter of claim 1, wherein the contact member is comprised of a plurality of intersecting beams.

6. The adapter of claim 5, wherein each of said beams is a diameter of the spout.

7. The adapter of claim 1, wherein the contact member includes a contact end located generally in an interior portion of the spout.

8. The adapter of claim 1, wherein each opening defines a quadrant within the spout.

9. An adapter mountable on an anesthetic agent container and configured to be received by an inlet port of an anesthetic vaporizer including a movable vaporizer valve assembly, the adapter comprising:
   a base engageable with an anesthetic agent container;
   a generally tubular spout extending upwardly from the base and including a contact member immovably attached to an interior portion of the spout and extending into the center of the spout, a top end of the spout located above a contact end of said contact member, and an adapter valve seat located below said contact member; and
   a movable adapter valve assembly received in the interior portion of the spout and including a plug biased against said adapter valve seat, and an elongated member operatively connected to said plug and extending above the top end of the spout when the plug is biased against said adapter valve seat, wherein said contact member is located to contact and move the movable vaporizer valve assembly when the adapter is inserted into the vaporizer inlet port, and wherein said plug is moved away from said adapter valve seat by contact between a contact end of said elongated member and a stationary portion of the inlet port when the spout is inserted into the inlet port.

10. The adapter of claim 9, further comprising a spline attached to an outer surface of said spout.

11. The adapter of claim 9, wherein the adapter is dimensioned so that the contact end of the contact member contacts the vaporizer valve assembly before the stationary portion of the inlet port contacts the contact end of the elongated member when the spout is inserted into the inlet port.

12. The adapter of claim 9, wherein the plug is biased against the adapter valve seat by a spring.

13. The adapter of claim 9, wherein the contact member is comprised of a plurality of intersecting beams.

14. The adapter of claim 13, wherein each of said beams is a diameter of the spout.

15. The adapter of claim 9, wherein the contact member includes a contact end located generally in the center of the spout.

* * * * *

UNITED STATES PATENT AND TRADEMARK OFFICE
CERTIFICATE OF CORRECTION

| | | |
|---|---|---|
| PATENT NO. | : 7,546,856 B2 | Page 1 of 1 |
| APPLICATION NO. | : 11/362693 | |
| DATED | : June 16, 2009 | |
| INVENTOR(S) | : David J. Chotenovsky | |

It is certified that error appears in the above-identified patent and that said Letters Patent is hereby corrected as shown below:

In Column 7, Line 43, change "abut" to --about--.

Signed and Sealed this

Twenty-third Day of March, 2010

David J. Kappos
*Director of the United States Patent and Trademark Office*